US012622930B2

(12) United States Patent
Park et al.

(10) Patent No.: US 12,622,930 B2
(45) Date of Patent: May 12, 2026

(54) PHARMACEUTICAL COMPOSITION FOR PREVENTING OR TREATING BRAIN DISEASE, COMPRISING STEM CELL-DERIVED EXOSOME SURFACE-MODIFIED WITH COMPOUND CAPABLE OF BINDING TO DOPAMINE RECEPTORS OR L-AMINO ACID TRANSPORTERS

(71) Applicant: RESEARCH & BUSINESS FOUNDATION SUNGKYUNKWAN UNIVERSITY, Suwon-si (KR)

(72) Inventors: Jae Hyung Park, Suwon-si (KR); Dong Gyu Jo, Suwon-si (KR); Sol Shin, Suwon-si (KR); Jae Hoon Sul, Anyang-si (KR)

(73) Assignee: RESEARCH & BUSINESS FOUNDATION SUNGKYUNKWAN UNIVERSITY, Suwon-si (KR)

( * ) Notice: Subject to any disclaimer, the term of this patent is extended or adjusted under 35 U.S.C. 154(b) by 581 days.

(21) Appl. No.: 18/105,355

(22) Filed: Feb. 3, 2023

(65) Prior Publication Data

US 2023/0241119 A1      Aug. 3, 2023

(30) Foreign Application Priority Data

Feb. 3, 2022      (KR) ........................ 10-2022-0014437
Feb. 1, 2023      (KR) ........................ 10-2023-0013690

(51) Int. Cl.
 *A61K 35/30*      (2015.01)
 *A61K 31/137*      (2006.01)
 *A61P 25/28*      (2006.01)

(52) U.S. Cl.
 CPC ............ *A61K 35/30* (2013.01); *A61K 31/137* (2013.01); *A61P 25/28* (2018.01)

(58) Field of Classification Search
 CPC ..................................................... A61K 31/198
 See application file for complete search history.

(56) References Cited

FOREIGN PATENT DOCUMENTS

WO      WO-2017054085 A1 *      4/2017      ............. C12N 15/87
WO      WO-2018011191 A1 *      1/2018      ............. A61P 37/00

OTHER PUBLICATIONS

Qu et al. "Dopamine-loaded blood exosomes targeted to brain for better treatment of Parkinson's disease" Journal of Controlled Release 287 (2018) 156-166 (Year: 2018).*
Sul et al. "Dopamine-conjugated extracellular vesicles induce autophagy in Parkinson's disease" J Extracell Vesicles. 2024;13:e70018 (Year: 2024).*

* cited by examiner

*Primary Examiner* — Thane Underdahl
(74) *Attorney, Agent, or Firm* — LEX IP MEISTER, PLLC

(57) ABSTRACT

The present disclosure relates to a pharmaceutical composition for preventing or treating a brain disease, comprising a stem cell-derived exosome surface-modified with a compound capable of binding to dopamine receptors or L-amino acid transporters as an active ingredient. The stem cell-derived exosome according to the present disclosure selectively binds to dopamine receptors (D2) overexpressed as autoreceptors in dopaminergic neurons in the substantia nigra through surface modification. Thereby, local accumulation in dopaminergic neurons is possible. In addition, it was identified that the stem cell-derived exosome exhibited an excellent neuron protective effect and neuron death inhibitory effect. Accordingly, the surface-modified stem cell-derived exosome according to the present disclosure is expected to be usefully used as a composition for preventing or treating a brain disease including Parkinson's disease and Alzheimer's disease.

8 Claims, 10 Drawing Sheets

PHARMACEUTICAL COMPOSITION FOR PREVENTING OR TREATING BRAIN DISEASE, COMPRISING STEM CELL-DERIVED EXOSOME SURFACE-MODIFIED WITH COMPOUND CAPABLE OF BINDING TO DOPAMINE RECEPTORS OR L-AMINO ACID TRANSPORTERS

CROSS-REFERENCE TO RELATED APPLICATION

This application claims priority to and the benefit of Korean Patent Application Nos. 10-2022-0014437 and 10-2023-0013690 filed on Feb. 3, 2022 and Feb. 1, 2023, respectively, and the disclosure of which is incorporated herein by reference in its entirety.

BACKGROUND

1. Field of the Invention

The present disclosure relates to a pharmaceutical composition for preventing or treating a brain disease, wherein the pharmaceutical composition comprises, as an active ingredient, a stem cell-derived exosome surface-modified with a compound capable of binding to dopamine receptors or L-amino acid transporters.

2. Discussion of Related Art

A degenerative brain disease refers to one of the degenerative diseases that develop in the brain with advancing years. It is known that the degenerative brain disease is caused by a decrease in the number of brain cells due to which certain brain cell groups in the brain and spinal cord gradually lose their functions for reasons unknown to date, death of the brain neurons, which are most important for the transmission of information in the brain nervous system, problems in the formation or function of synapses that transmit information between brain neurons, and abnormal symptoms or reduction in electrical activity of the cranial nerves. Examples of representative diseases include Alzheimer's disease, Parkinson's disease, Huntington's disease, and amyotrophic lateral sclerosis.

Parkinson's disease is a neurodegenerative brain disease caused by a deficiency of dopamine in the nigro-striatal pathway as a result of specific loss of dopaminergic neurons in the substantia nigra in the midbrain area and catecholamine neurons in the brainstem, resulting in motor function abnormalities such as tremors, muscle stiffness, and bradykinesia, in which body movements are slowed down. In the current treatment method, drug treatment and exercise therapy are preceded by symptomatic therapy, and surgery is performed for late patients who do not show appropriate efficacy of drug treatment. Drug treatment relieves symptoms for a while by using dopamine precursors (levodopa) and dopamine agonists to replenish the deficient dopamine and delay the loss of dopamine in the brain, but it does not stop the degeneration and loss of dopaminergic neurons. Therefore, a fundamental treatment method is required.

Exosomes are membrane vesicles with a size of 50-200 nm that are secreted from cells and are mostly present in bodily fluids including blood and urine, carry cell-specific constituents accounting for unique biological functions of cells of origin (donor cell), and include various watersoluble proteins, peripheral proteins, and transmembrane protein components in addition to phospholipids, mRNA, miRNA, and DNA.

Exosomes have lipid bilayers that are the same phospholipid bilayer structure as in source cells (donor cells), and are compositions of substances extracellularly excreted by cells, delivering physiologically active substances to receptor cells and acting as signal transduction mediators that control cell functions such as cell-cell communication and cellular immune intervention.

In particular, it is known that "stem cell-derived exosomes" secreted from stem cells contain various physiologically active factors and genetic materials and may control cell behavior regulation, stem cell differentiation, and tissue regeneration.

Transplant therapy using stem cells is currently in the clinical stage, and it is known that the injected stem cells differentiate into dopaminergic neurons to replace damaged neurons or suppress peripheral inflammatory responses to exhibit therapeutic effects. However, in vitro differentiation is possible, but there is an issue that the engraftment rate and differentiation efficiency of transplanted cells are low. Furthermore, there are difficulties in the clinical stage due to limitations such as permanent damage caused by invasive procedures accompanying transplantation of stem cells, risk of cancerization of transplanted cells and intractable immune response, and infection by fetal bovine serum used in cell culture stage.

However, stem cell-derived exosomes are known to be rich in bioactive factors secreted from stem cells, so they can replace the functions of parent cells, have a cell membrane-like structure, have high biocompatibility, and may pass through the blood-brain barrier. It is expected to form a new treatment method paradigm that may solve the issues of existing stem cell-based therapeutic agents, such as low survival rate and differentiation rate of cells injected into the body and tissue calcification. However, in general, when injected into the body, less than 1% of Naïve exosomes reach the brain, so an efficient intracerebral delivery method is required to use exosome therapeutic agents for brain diseases.

In this regard, the present inventors, as a method for increasing the efficiency and efficacy of drugs through efficient intracerebral drug delivery in the treatment of brain diseases, attempted to enable local accumulation in dopaminergic neurons by modifying the surface of exosomes with ligands to selectively bind to dopamine receptors (D2) overexpressed as autoreceptors in dopaminergic neurons in the substantia nigra.

SUMMARY OF THE INVENTION

The present inventors specifically targeted dopaminergic neurons by modifying the surface of stem cell-derived exosomes using a compound capable of binding to dopamine receptors or L-amino acid transporters, and prepared surface-modified stem cell-derived exosomes that have a preventive or therapeutic effect on brain diseases such as Parkinson's disease by exhibiting neuroprotective effects and inhibitory effects on neuron death, and then completed the present disclosure based thereon.

In this regard, an aspect of the present disclosure is to provide a pharmaceutical composition for preventing or treating a brain disease, comprising a stem cell-derived exosome as an active ingredient, wherein the stem cell-derived exosome is surface-modified with a compound capable of binding to dopamine receptors or L-amino acid transporters.

Technical objects to be achieved by the present disclosure are not limited to the aforementioned technical objects, and other technical objects not described above may be evidently understood by a person having ordinary skill in the art to which the present disclosure pertains from the following description.

An aspect of the present disclosure is to provide a pharmaceutical composition for preventing or treating a brain disease, comprising a stem cell-derived exosome as an active ingredient, wherein the stem cell-derived exosome is surface-modified with a compound capable of binding to dopamine receptors or L-amino acid transporters.

In addition, an embodiment of the present disclosure provides a method for preparing a stem cell-derived exosome surface-modified with a compound capable of binding to dopamine receptors or L-amino acid transporters, wherein the method comprises the following steps:

(a) extracting exosomes from stem cells; and (b) adding the compound capable of binding to dopamine receptors or L-amino acid transporters and stirring the same.

In addition, an embodiment of the present disclosure provides a stem cell-derived exosome surface-modified with a compound capable of binding to dopamine receptors or L-amino acid transporters, wherein the exosome has a targeting ability for dopaminergic neurons and has a neuroprotective activity.

In an embodiment of the present disclosure, the stem cells may be one or more selected from the group consisting of adipose-derived stem cells, umbilical cord blood stem cells, bone marrow stem cells, neural stem cells, muscle stem cells, skin stem cells, and amnion stem cells, but not limited thereto.

As another embodiment of the present disclosure, the compound capable of binding to dopamine receptors or L-amino acid transporters may be dopamine or a dopamine precursor, but is not limited thereto.

As yet another embodiment of the present disclosure, the dopamine precursor may be one or more selected from the group consisting of levodopa (L-dopa), L-phenylalanine, L-tyrosine, phenylethylamine, and tyramine, but is not limited thereto.

As yet another embodiment of the present disclosure, the stem cell-derived exosome may have a targeting ability for dopaminergic neurons, but is not limited thereto.

As yet another embodiment of the present disclosure, the stem cell-derived exosome may have a neuroprotective activity, but is not limited thereto.

As yet another embodiment of the present disclosure, the brain disease may be one or more selected from the group consisting of Parkinson's disease, Alzheimer's disease, dementia, Huntington's disease, amyotrophic lateral sclerosis, multiple sclerosis, Creutzfeldt-Jakob disease, Pick disease, and Lewy body disease, but is not limited thereto.

As yet another embodiment of the present disclosure, the stem cell-derived exosome may be surface-modified through one or more chemical bonds selected from the group consisting of ionic bonds, covalent bonds, metal bonds, coordination bonds, hydrogen bonds, and intermolecular forces between exosome surface proteins and the compound capable of binding to dopamine receptors or L-amino acid transporters; or hydrophobic insertion of amphiphilic compound bound to the compound capable of binding to dopamine receptors or L-amino acid transporters into phospholipid bilayer of the exosome, but is not limited thereto.

As yet another embodiment of the present disclosure, the compound capable of binding to dopamine receptors or L-amino acid transporters may be bound to a surface of the exosome at a dry weight ratio of 1:0.0005 to 0.005 (the exosome:the compound capable of binding to dopamine receptors or L-amino acid transporters) with respect to a dry weight of the exosome, but is not limited thereto.

In addition, an embodiment of the present disclosure provides a method for preventing or treating a brain disease, comprising administering to a subject in need thereof a composition comprising, as an active ingredient, a stem cell-derived exosome surface-modified with a compound capable of binding to dopamine receptors or L-amino acid transporters.

In addition, an embodiment of the present disclosure provides a use of a composition comprising, as an active ingredient, a stem cell-derived exosome surface-modified with a compound capable of binding to dopamine receptors or L-amino acid transporters for preventing or treating a brain disease.

In addition, an embodiment of the present disclosure provides a use of a stem cell-derived exosome surface-modified with a compound capable of binding to dopamine receptors or L-amino acid transporters for preparing drugs for treating a brain disease.

BRIEF DESCRIPTION OF THE DRAWINGS

FIG. 2A is a diagram identifying the particle size and shape of a stem cell-derived exosome surface-modified with a compound capable of binding to dopamine receptors or L-amino acid transporters according to an embodiment of the present disclosure before and after modification.

FIG. 2B is a diagram identifying whether the stem cell-derived exosome surface-modified with a compound capable of binding to dopamine receptors or L-amino acid transporters according to an embodiment of the present disclosure is modified and the dopamine content on the surface.

DETAILED DESCRIPTION OF EXEMPLARY EMBODIMENTS

Figure 1:
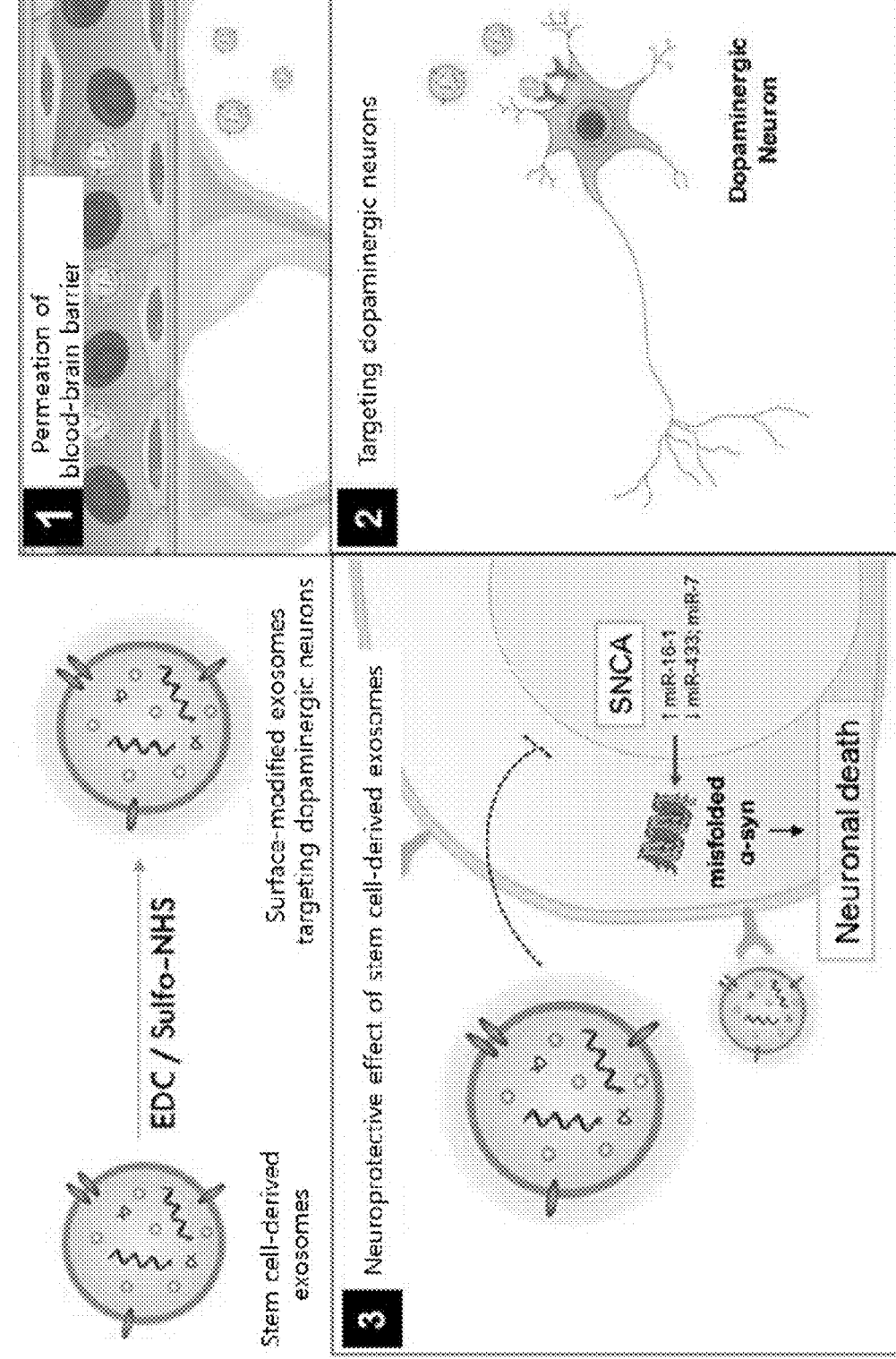
FIG. 1 is a schematic diagram showing the action of a stem cell-derived exosome surface-modified with a compound capable of binding to dopamine receptors or L-amino acid transporters according to an embodiment of the present disclosure.

In an embodiment of the present disclosure, exosomes were extracted from human adipose-derived stem cells (see Example 1), and the surface of the stem cell-derived exosomes was modified using a compound capable of binding to dopamine receptors or L-amino acid transporters (see Example 2).

In another embodiment of the present disclosure, it was observed that a stem cell-derived exosome surface-modified with a compound capable of binding to dopamine receptors or L-amino acid transporters was effectively absorbed to dopamine receptor-expressing cells, indicating that it had excellent targeting ability to neurons (see Example 3).

In another embodiment of the present disclosure, an in vitro Parkinson's disease cell model clinically most similar to Parkinson's disease was induced by treating preformed-fibril (PFF), which allows the formation of alpha synuclein aggregates and hyperphosphorylation (p-a-syn), and it was identified that a stem cell-derived exosome surface-modified with a compound capable of binding to dopamine receptors or L-amino acid transporters exhibited apoptosis reduction and neuroprotective effects. Among them, it was identified that a stem cell-derived exosome surface-modified with dopamine inhibited hyperphosphorylation of alpha synuclein, a marker of Parkinson's disease, and this effect disappeared by exosomal degradation upon ultrasonic treatment. In addition, it was identified that when the surface-modified stem cell-derived exosome was administered to mice, migration to the brain and accumulation in the brain increased compared to the case where the surface-unmodified exosome was administered (see Example 4).

In this regard, an embodiment of the present disclosure provides a pharmaceutical composition for preventing or treating a brain disease, comprising a stem cell-derived exosome as an active ingredient, wherein the stem cell-derived exosome is surface-modified with a compound capable of binding to dopamine receptors or L-amino acid transporters.

As used herein, the term "stem cell" refers to a general concept of undifferentiated cells having the ability to differentiate into various types of tissue cells, that is, undifferentiated cells having stemness, and includes both multipotency and unipotency as well as pluripotency capable of differentiating into all types of cells configuring constituting living organisms such as nerves, blood, and cartilage. These stem cells are roughly divided into embryonic stem cells which may be produced using embryos, adult stem cells, germ cells (gametes), cancer stem cells, and the like, the embryonic stem cells refer to a stage of a cell mass before foiling a specific organ in less than 14 days after fertilization, and recently, embryonic stem cells are also produced from normal cells through dedifferentiation. Accordingly, the stem cells are not limited thereto as long as the stem cells are cells capable of differentiating into all cells and tissues constituting the body. Adult stem cells are extracted from umbilical cord blood, bone marrow, fat, blood and the like, and refer to primitive cells just before differentiation into cells of specific organs such as bone, liver and blood. Germ cells are cells that transmit genetic information to the next generation through reproduction, and although human beings have sperm and ova, germ cells are not limited thereto.

In addition, stem cells may self-replicate in the process of forming clones to form cell clusters to maintain a new stem cell in the cluster, and have the ability to form one or more characteristic cell types through differentiation.

In an embodiment of the present disclosure, the stem cells may be one or more selected from the group consisting of adipose-derived stem cells, umbilical cord blood stem cells, bone marrow stem cells, neural stem cells, muscle stem cells, skin stem cells, and amnion stem cells. According to an embodiment of the present disclosure, the stem cells may be human-derived adipose-derived stem cells, but is not limited thereto.

In an embodiment of the present disclosure, the term "adipose-derived stem cells (ASCs)" refers to stem cells extracted from fat among adult stem cells of various origins such as bone, muscle, fat, and umbilical cord blood. The adipose-derived stem cells (ASCs) with multipotency may differentiate into most mesenchymal cells, such as adipocytes, osteoblasts, chondroblasts, and myofibroblasts.

In an embodiment of the present disclosure, the term "exosomes" refers to membrane-structured small vesicles secreted from various cells. The exosomes are not directly detached from the plasma membrane, but originate from specific intracellular compartments called multivesicular bodies (MVBs) and are released and secreted out of cells, as observed in research through electron microscopy. In other words, when MVBs are fused with the plasma membrane, the vesicles are released into an extracellular environment, which are called exosomes. Although it has not been clearly known by which molecular mechanism these exosomes are produced, it has been known that various types of immune cells including B-lymphocytes, T-lymphocytes, dendritic cells, thrombocytes and macrophages as well as erythrocytes, tumor cells, and stem cells produce and secrete exosomes in a living state. The exosomes are naturally secreted or artificially produced.

Such exosomes are released from all animal cells such as mast cells, lymphocytes, astrocytes, platelets, neurons, endothelial cells, epithelial cells, etc. and are found in various body fluids including blood, urine, mucus, saliva, bile juice, ascitic fluid, cerebrospinal fluid, and so on. Exhibiting high selective penetration sufficient to cross even the blood-brain barrier (BBB) as well as cell membranes of epidermal and endothelial cells, exosomes can find applications in the development of drug delivery systems utilizing nanocarriers for specific drugs.

In an embodiment of the present disclosure, the exosome may have a diameter of 10 nm to 500 nm, 10 nm to 400 nm, 10 nm to 300 nm, 10 nm to 250 nm, 10 nm to 200 nm, 10 nm to 150 nm, 50 nm to 500 nm, 50 nm to 400 nm, 50 nm to 300 nm, 50 nm to 200 nm, 50 nm to 150 nm, 100 nm to 500 nm, 100 nm to 400 nm, 100 nm to 300 nm, or 150 nm to 250 nm, but is not limited thereto.

In an embodiment of the present disclosure, the exosome may include $1\times10^4$ to $1\times10^9$, $1\times10^4$ to $1\times10^8$, $5\times10^4$ to $1\times10^9$, $5\times10^4$ to $1\times10^8$, $1\times10^5$ to $1\times10^9$, $1\times10^5$ to $1\times10^8$, $1\times10^6$ to $1\times10^9$, $1\times10^6$ to $1\times10^8$, $1\times10^7$ to $1\times10^9$, $1\times10^7$ to $1\times10^8$, $1\times10^5$, $1\times10^6$, $1\times10^7$, or $1\times10^8$ per milliliter of the composition, but is not limited thereto.

In an embodiment of the present disclosure, the compound capable of binding to dopamine receptors or L-amino acid transporters may be dopamine or a dopamine precursor, but is not limited thereto.

In an embodiment of the present disclosure, the term "dopamine" refers to a chemical substance with catecholamine, and dopamine acts as a neurotransmitter in the brain. Dopamine neurons secreting dopamine are located in the ventral tegmental area of the midbrain, the substantia nigra, and the arcuate nucleus of hypothalamus. In dopamine-secreting neurons, levodopa (L-DOPA) is synthesized from tyrosine using tyrosine hydroxylase, and DOPA decarboxylase is used to remove a carboxyl group to produce dopamine Dopamine exerts its action through cell membrane receptors. There are five types of dopamine receptors, from D1 to D5. Among them, D1 and D5 are called D1-like and activate Gs protein-dependent signaling mechanisms. D2, D3, and D4 are called D2-like and activate Gi/Go protein-dependent signaling mechanisms. Accordingly, dopamine is both excitatory (D1-like action) and inhibitory (D2-like action), depending on which dopamine receptors expressed on which cells it acts on.

In an embodiment of the present disclosure, the term "dopamine precursor" refers to products in the intermediate stages required for the final synthesis of dopamine in vivo, and may include any and all possible isomers, stereoisomers, enantiomers, diastereomers, tautomers, pharmaceutically acceptable salts, hydrates, and solvates.

In an embodiment of the present disclosure, the dopamine precursor may be one or more selected from the group consisting of levodopa (L-dopa), L-phenylalanine, L-tyrosine, phenylethylamine, and tyramine, but is not limited thereto.

In an embodiment of the present disclosure, the term "surface modification" refers to configuring a modified layer through a method such as binding or coating a compound capable of binding to dopamine receptors or L-amino acid transporters to the surface of exosomes, wherein the bond may be a chemical bond including an ionic bond, a covalent bond, a metal bond, a coordination bond, a hydrogen bond, and an intermolecular force. According to an embodiment of the present disclosure, a compound capable of binding to dopamine receptors or L-amino acid transporters may be bound to the surface of exosomes through chemical bonds between the carboxyl group (—COOH) of the stem cell-derived exosome surface protein and the amine group (—NH$_2$) of a compound capable of binding to the dopamine receptors or L-amino acid transporters. However, when the surface of the exosome may be modified, there is no limitation on the surface modification method.

In an embodiment of the present disclosure, the surface modification method may comprise a method of directly binding a compound capable of binding to dopamine receptors or L-amino acid transporters to the surface of exosomes, or a method of modifying the surface of exosomes with a compound capable of binding to dopamine receptors or L-amino acid transporters by binding a compound capable of binding to dopamine receptors or L-amino acid transporters to an amphiphilic compound and then performing hydrophobic insertion of the amphiphilic compound into phospholipid bilayer of the exosomes.

In an embodiment of the present disclosure, the amphiphilic compound may be an amphiphilic compound capable of inserting into phospholipid bilayer of the exosomes, for example, one or more selected from the group consisting of 1,2-Distearoyl-sn-glycero-3-phosphoethanolamine (DSPE), Polyethylene glycol (PEG), transmembrane protein, cholesterol, phospholipid (Ceramide, Sphingomyelin, etc.), and C18, but is not limited thereto.

In an embodiment of the present disclosure, the compound capable of binding to dopamine receptors or L-amino acid transporters may be bound to the surface of exosomes in a dry weight ratio of 1:0.0005 to 0.005, 1:0.0005 to 0.004, 1:0.0005 to 0.003, 1:0.0005 to 0.0025, 1:0.001 to 0.005, 1:0.001 to 0.004, 1:0.001 to 0.003, 1:0.001 to 0.0025, 1:0.002 to 0.005, 1:0.002 to 0.004, 1:0.002 to 0.003, or 1:0.0015 to 0.0025 (exosome:a compound capable of binding to dopamine receptors or L-amino acid transporters) with respect to a dry weight of exosomes based on 0.33 μg/ml of protein in the aqueous solution containing exosomes, but is not limited thereto.

In an embodiment of the present disclosure, the stem cell-derived exosome surface-modified with a compound capable of binding to dopamine receptors or L-amino acid transporters has a targeting ability for dopaminergic neurons, and selectively binds to dopamine receptors (D2) overexpressed as autoreceptors in dopaminergic neurons in the substantia nigra. Thereby, local accumulation in dopaminergic neurons is possible. In addition, it may have neuron death inhibition and neuron protective activity.

In an embodiment of the present disclosure, the term "targeting ability" refers to the ability of a stem cell-derived exosome surface-modified with a compound capable of binding to dopamine receptors or L-amino acid transporters to specifically migrate to dopaminergic neurons.

In an embodiment of the present disclosure, the term "brain disease" includes all diseases caused by abnormality of brain, for example, the brain disease includes a degenerative brain disease. In an embodiment of the present disclosure, the term "degenerative brain disease" refers to a brain disease caused by damage to neurons, and is assumed to be caused by aging, genetic mutations, stress, and problems with the function of removing proteins in cells, but the exact cause has not been identified. The brain disease may be, for example, one or more selected from the group consisting of Parkinson's disease, Alzheimer's disease, dementia, Huntington's disease, amyotrophic lateral sclerosis, multiple sclerosis, Creutzfeldt-Jakob disease, Pick disease, and dementia with Lewy bodies. According to an embodiment of the present disclosure, the brain disease may be caused by alpha synuclein, but is not limited thereto.

In addition, a stem cell-derived exosome surface-modified with a compound capable of binding to dopamine receptors or L-amino acid transporters according to an embodiment of the present disclosure may be used for prevention or treatment of diseases caused by brain diseases in addition to the brain diseases, such as depression, motor symptoms, dysosmia, insomnia, and dementia, and may also be used for prevention or treatment of complications caused by brain diseases, such as urinary or fecal incontinence, gait disorder, body stiffness, pneumonia, pressure sores, etc.

The pharmaceutical composition according to the present invention may further include a suitable carrier, excipient, and diluent which are commonly used in the preparation of pharmaceutical compositions. The excipient may be, for example, one or more selected from the group consisting of a diluent, a binder, a disintegrant, a lubricant, an adsorbent, a humectant, a film-coating material, and a controlled release additive.

The pharmaceutical composition according to the present invention may be used by being formulated, according to commonly used methods, into a form such as powders, granules, sustained-release-type granules, enteric granules, liquids, eye drops, elixirs, emulsions, suspensions, spirits, troches, aromatic water, lemonades, tablets, sustained-release-type tablets, enteric tablets, sublingual tablets, hard capsules, soft capsules, sustained-release-type capsules, enteric capsules, pills, tinctures, soft extracts, dry extracts, fluid extracts, injections, capsules, perfusates, or a preparation for external use, such as plasters, lotions, pastes, sprays, inhalants, patches, sterile injectable solutions, or aerosols. The preparation for external use may have a formulation such as creams, gels, patches, sprays, ointments, plasters, lotions, liniments, pastes, or cataplasmas.

As the carrier, the excipient, and the diluent that may be included in the pharmaceutical composition according to the present invention, lactose, dextrose, sucrose, oligosaccharides, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil may be used.

For formulation, commonly used diluents or excipients such as fillers, thickeners, binders, wetting agents, disintegrants, and surfactants are used.

As additives of tablets, powders, granules, capsules, pills, and troches according to the present invention, excipients such as corn starch, potato starch, wheat starch, lactose, white sugar, glucose, fructose, D-mannitol, precipitated calcium carbonate, synthetic aluminum silicate, dibasic calcium phosphate, calcium sulfate, sodium chloride, sodium hydrogen carbonate, purified lanolin, microcrystalline cellulose, dextrin, sodium alginate, methyl cellulose, sodium carboxymethylcellulose, kaolin, urea, colloidal silica gel, hydroxypropyl starch, hydroxypropyl methylcellulose (HPMC), HPMC 1928, HPMC 2208, HPMC 2906, HPMC 2910, propylene glycol, casein, calcium lactate, and Primojel®; and binders such as gelatin, Arabic gum, ethanol, agar powder, cellulose acetate phthalate, carboxymethylcellulose, calcium carboxymethylcellulose, glucose, purified water, sodium caseinate, glycerin, stearic acid, sodium carboxymethylcellulose, sodium methylcellulose, methylcellulose, microcrystalline cellulose, dextrin, hydroxycellulose, hydroxypropyl starch, hydroxymethylcellulose, purified shellac, starch, hydroxypropyl cellulose, hydroxypropyl methylcellulose, polyvinyl alcohol, and polyvinylpyrrolidone may be used, and disintegrants such as hydroxypropyl methylcellulose, corn starch, agar powder, methylcellulose, bentonite, hydroxypropyl starch, sodium carboxymethylcellulose, sodium alginate, calcium carboxymethylcellulose, calcium citrate, sodium lauryl sulfate, silicic anhydride, 1-hydroxypropylcellulose, dextran, ion-exchange resin, polyvinyl acetate, formaldehyde-treated casein and gelatin, alginic acid, amylose, guar gum, sodium bicarbonate, polyvinylpyrrolidone, calcium phosphate, gelled starch, Arabic gum, amylopectin, pectin, sodium polyphosphate, ethyl cellulose, white sugar, magnesium aluminum silicate, a disorbitol solution, and light anhydrous silicic acid; and lubricants such as calcium stearate, magnesium stearate, stearic acid, hydrogenated vegetable oil, talc, lycopodium powder, kaolin, Vaseline, sodium stearate, cacao butter, sodium salicylate, magnesium salicylate, polyethylene glycol (PEG)

4000, PEG 6000, liquid paraffin, hydrogenated soybean oil (Lubri wax), aluminum stearate, zinc stearate, sodium lauryl sulfate, magnesium oxide, Macrogol, synthetic aluminum silicate, silicic anhydride, higher fatty acids, higher alcohols, silicone oil, paraffin oil, polyethylene glycol fatty acid ether, starch, sodium chloride, sodium acetate, sodium oleate, dl-leucine, and light anhydrous silicic acid may be used.

As additives of liquids according to the present invention, water, dilute hydrochloric acid, dilute sulfuric acid, sodium citrate, monostearic acid sucrose, polyoxyethylene sorbitol fatty acid esters (twin esters), polyoxyethylene monoalkyl ethers, lanolin ethers, lanolin esters, acetic acid, hydrochloric acid, ammonia water, ammonium carbonate, potassium hydroxide, sodium hydroxide, prolamine, polyvinylpyrrolidone, ethylcellulose, and sodium carboxymethylcellulose may be used.

In syrups according to the present invention, a white sugar solution, other sugars or sweeteners, and the like may be used, and as necessary, a fragrance, a colorant, a preservative, a stabilizer, a suspending agent, an emulsifier, a viscous agent, or the like may be used.

In emulsions according to the present invention, purified water may be used, and as necessary, an emulsifier, a preservative, a stabilizer, a fragrance, or the like may be used.

In suspensions according to the present invention, suspending agents such as acacia, tragacanth, methylcellulose, carboxymethylcellulose, sodium carboxymethylcellulose, microcrystalline cellulose, sodium alginate, hydroxypropyl methylcellulose (HPMC), HPMC 1828, HPMC 2906, HPMC 2910, and the like may be used, and as necessary, a surfactant, a preservative, a stabilizer, a colorant, and a fragrance may be used.

Injections according to the present invention may include: solvents such as distilled water for injection, a 0.9% sodium chloride solution, Ringer's solution, a dextrose solution, a dextrose+sodium chloride solution, PEG, lactated Ringer's solution, ethanol, propylene glycol, non-volatile oil-sesame oil, cottonseed oil, peanut oil, soybean oil, corn oil, ethyl oleate, isopropyl myristate, and benzene benzoate; cosolvents such as sodium benzoate, sodium salicylate, sodium acetate, urea, urethane, monoethylacetamide, butazolidine, propylene glycol, the Tween series, amide nicotinate, hexamine, and dimethylacetamide; buffers such as weak acids and salts thereof (acetic acid and sodium acetate), weak bases and salts thereof (ammonia and ammonium acetate), organic compounds, proteins, albumin, peptone, and gums; isotonic agents such as sodium chloride; stabilizers such as sodium bisulfite ($NaHSO_3$) carbon dioxide gas, sodium metabisulfite ($Na_2S_2O_5$), sodium sulfite ($Na_2SO_3$), nitrogen gas ($N_2$), and ethylenediamine tetraacetic acid; sulfating agents such as 0.1% sodium bisulfide, sodium formaldehyde sulfoxylate, thiourea, disodium ethylenediaminetetraacetate, and acetone sodium bisulfite; a pain relief agent such as benzyl alcohol, chlorobutanol, procaine hydrochloride, glucose, and calcium gluconate; and suspending agents such as sodium CMC, sodium alginate, Tween 80, and aluminum monostearate.

In suppositories according to the present invention, bases such as cacao butter, lanolin, Witepsol, polyethylene glycol, glycerogelatin, methylcellulose, carboxymethylcellulose, a mixture of stearic acid and oleic acid, Subanal, cottonseed oil, peanut oil, palm oil, cacao butter+cholesterol, lecithin, lanette wax, glycerol monostearate, Tween or span, imhausen, monolan (propylene glycol monostearate), glycerin, Adeps solidus, buytyrum Tego-G, cebes Pharma 16, hexalide base 95, cotomar, Hydrokote SP, S-70-XXA, S-70-

XX75 (S-70-XX95), Hydrokote 25, Hydrokote 711, idropostal, massa estrarium (A, AS, B, C, D, E, I, T), masa-MF, masupol, masupol-15, neosuppostal-N, paramount-B, supposiro OSI, OSIX, A, B, C, D, H, L, suppository base IV types AB, B, A, BC, BBG, E, BGF, C, D, 299, suppostal N, Es, Wecoby W, R, S, M, Fs, and tegester triglyceride matter (TG-95, MA, 57) may be used.

Solid preparations for oral administration include tablets, pills, powders, granules, capsules, and the like, and such solid preparations are formulated by mixing the composition with at least one excipient, e.g., starch, calcium carbonate, sucrose, lactose, gelatin, and the like. In addition to simple excipients, lubricants such as magnesium stearate and talc are also used.

Examples of liquid preparations for oral administration include suspensions, liquids for internal use, emulsions, syrups, and the like, and these liquid preparations may include, in addition to simple commonly used diluents, such as water and liquid paraffin, various types of excipients, for example, a wetting agent, a sweetener, a fragrance, a preservative, and the like. Preparations for parenteral administration include an aqueous sterile solution, a non-aqueous solvent, a suspension, an emulsion, a freeze-dried preparation, and a suppository. Non-limiting examples of the non-aqueous solvent and the suspension include propylene glycol, polyethylene glycol, a vegetable oil such as olive oil, and an injectable ester such as ethyl oleate.

The pharmaceutical composition according to the present invention is administered in a pharmaceutically effective amount. In the present invention, "the pharmaceutically effective amount" refers to an amount sufficient to treat diseases at a reasonable benefit/risk ratio applicable to medical treatment, and an effective dosage level may be determined according to factors including types of diseases of patients, the severity of disease, the activity of drugs, sensitivity to drugs, administration time, administration route, excretion rate, treatment period, and simultaneously used drugs, and factors well known in other medical fields.

The composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this may be easily determined by those of ordinary skill in the art.

The pharmaceutical composition of the present invention may be administered to a subject via various routes. All administration methods can be predicted, and the pharmaceutical composition may be administered via, for example, oral administration, subcutaneous injection, intraperitoneal injection, intravenous injection, intramuscular injection, intrathecal (space around the spinal cord) injection, sublingual administration, administration via the buccal mucosa, intrarectal insertion, intravaginal insertion, ocular administration, intra-aural administration, intranasal administration, inhalation, spraying via the mouth or nose, transdermal administration, percutaneous administration, or the like.

The pharmaceutical composition of the present invention is determined depending on the type of a drug, which is an active ingredient, along with various related factors such as a disease to be treated, administration route, the age, gender, and body weight of a patient, and the severity of diseases.

As another aspect of the present disclosure, an embodiment of the present disclosure provides a food composition for preventing or alleviating a brain disease, comprising a stem cell-derived exosome as an active ingredient, wherein the stem cell-derived exosome is surface-modified with a compound capable of binding to dopamine receptors or L-amino acid transporters.

In an embodiment of the present disclosure, the food composition may be a health functional food composition, but is not limited thereto.

The stem cell-derived exosome surface-modified with a compound capable of binding to dopamine receptors or L-amino acid transporters according to the present invention may be used by adding the exosome as is to food or may be used together with other foods or food ingredients, but may be appropriately used according to a typical method. The mixed amount of the active ingredient may be suitably determined depending on the purpose of use thereof (for prevention or alleviation). In general, when a food or beverage is prepared, the exosome of the present invention is added in an amount of 15 wt % or less, preferably 10 wt % or less based on the raw materials. However, for long-term intake for the purpose of health and hygiene or for the purpose of health control, the amount may be less than the above-mentioned range, and the vesicles have no problem in terms of stability, so the active ingredient may be used in an amount more than the above-mentioned range.

The type of food is not particularly limited. Examples of food to which the material may be added include meats, sausage, bread, chocolate, candies, snacks, confectioneries, pizza, instant noodles, other noodles, gums, dairy products including ice creams, various soups, beverages, tea, drinks, alcoholic beverages, vitamin complexes, and the like, and include all health functional foods in a typical sense.

The health beverage composition according to the present invention may contain various flavors or natural carbohydrates, and the like as additional ingredients as in a typical beverage. The above-described natural carbohydrates may be monosaccharides such as glucose and fructose, disaccharides such as maltose and sucrose, polysaccharides such as dextrin and cyclodextrin, and sugar alcohols such as xylitol, sorbitol, and erythritol. As a sweetener, it is possible to use a natural sweetener such as thaumatin and stevia extract, a synthetic sweetener such as saccharin and aspartame, and the like. The proportion of the natural carbohydrates is generally about 0.01 to 0.20 g, or about 0.04 to 0.10 g per 100 ml of the composition of the present invention.

In addition to the aforementioned ingredients, the composition of the present invention may contain various nutrients, vitamins, electrolytes, flavors, colorants, pectic acids and salts thereof, alginic acid and salts thereof, organic acids, protective colloid thickeners, pH adjusters, stabilizers, preservatives, glycerin, alcohols, carbonating agents used in carbonated drinks, and the like. In addition, the composition of the present invention may contain flesh for preparing natural fruit juice, fruit juice drinks, and vegetable drinks. These ingredients may be used either alone or in combinations thereof. The proportion of these additives is not significantly important, but is generally selected within a range of 0.01 to 0.20 part by weight per 100 parts by weight of the composition of the present invention.

In yet another aspect of the present disclosure, an embodiment of the present disclosure provides a method for preventing, treating, or alleviating a brain disease, comprising administering to a subject in need thereof a composition comprising, as an active ingredient, a stem cell-derived exosome, wherein the stem cell-derived exosome is surface-modified with a compound capable of binding to dopamine receptors or L-amino acid transporters.

In yet another aspect of the present disclosure, an embodiment of the present disclosure provides a method for preventing, treating, or alleviating a brain disease, comprising administering to a subject in need thereof a composition comprising, as an active ingredient, a stem cell-derived exosome surface-modified with a compound capable of binding to dopamine receptors or L-amino acid transporters.

In yet another aspect of the present disclosure, an embodiment of the present disclosure provides a use of a composition comprising, as an active ingredient, a stem cell-derived exosome surface-modified with a compound capable of binding to dopamine receptors or L-amino acid transporters for preventing, treating, or alleviating a brain disease.

In yet another aspect of the present disclosure, an embodiment of the present disclosure provides a use of a stem cell-derived exosome surface-modified with a compound capable of binding to dopamine receptors or L-amino acid transporters for preparing drugs for treating a brain disease.

As used herein, the "subject" refers to a subject in need of treatment of a disease, and more specifically, refers to a mammal such as a human or a non-human primate, a mouse, a rat, a dog, a cat, a horse, and a cow, but the present invention is not limited thereto.

As used herein, the "administration" refers to providing a subject with a predetermined composition of the present invention by using an arbitrary appropriate method.

The term "prevention" as used herein means all actions that inhibit or delay the onset of a target disease. The term "treatment" as used herein means all actions that alleviate or beneficially change a target disease and abnormal metabolic symptoms caused thereby via administration of the pharmaceutical composition according to the present invention. The term "improvement" as used herein means all actions that reduce the degree of parameters related to a target disease, e.g., symptoms via administration of the composition according to the present invention.

In yet another aspect of the present disclosure, an embodiment of the present disclosure provides a method for preparing a stem cell-derived exosome surface-modified with a compound capable of binding to dopamine receptors or L-amino acid transporters, wherein the method comprises the following steps:

(a) extracting exosomes from stem cells; and (b) adding the compound capable of binding to dopamine receptors or L-amino acid transporters and stirring the same.

In an embodiment of the present disclosure, the step (b) may comprise adding the compound capable of binding to dopamine receptors or L-amino acid transporters, stirring the same, and then binding the compound capable of binding to dopamine receptors or L-amino acid transporters to exosome surface proteins.

At this time, the method may further comprise adding N-hydroxysulfosuccinimide (Sulfo-NHS) and 1-ethyl-3-(3-dimethylamino-propyl) carbodiimide (EDC) to the extracted stem cell-derived exosomes and stirring the same before step (b), and the method may further comprise removing unreacted Sulfo-NHS, EDC, and the compound capable of binding to dopamine receptors or L-amino acid transporters through a filter after step (b), but is not limited thereto.

In an embodiment of the present disclosure, the step (b) may comprise binding a compound capable of binding to dopamine receptors or L-amino acid transporters to an amphiphilic compound capable of hydrophobic inserting into phospholipid bilayer of the exosomes, adding and stirring the same, and then performing hydrophobic insertion of the amphiphilic compound into phospholipid bilayer of the exosomes.

At this time, the amphiphilic compound may be directly bound to the compound capable of binding to dopamine receptors or L-amino acid transporters or bound through a linker, and the type of the linker is not limited.

In an embodiment of the present disclosure, in the step of adding and stirring Sulfo-NHS and EDC, the exosomes may be exosomes dispersed in PBS. The stirring may be performed for 10 to 60 minutes, 10 to 50 minutes, 10 to 40 minutes, 10 to 30 minutes, 20 to 60 minutes, 20 to 50 minutes, 20 to 40 minutes, 20 to 30 minutes, 30 to 60 minutes, 30 to 50 minutes, 30 to 40 minutes, or 30 minutes, but is not limited thereto.

In an embodiment of the present disclosure, in step (b), the stirring may be performed for 1 to 12 hours, 1 to 10 hours, 1 to 8 hours, 1 to 6 hours, 3 to 12 hours, 3 to 10 hours, 3 to 8 hours, 3 to 6 hours, 5 to 12 hours, 5 to 10 hours, 5 to 8 hour, 5 to 6 hours, or 6 hours at 0 to 15° C., 0 to 13° C., 0 to 11° C., 0 to 9° C., 0 to 7° C., 0 to 5° C., 2 to 15° C., 2 to 13° C., 2 to 11° C., 2 to 9° C., 2 to 7° C., 2 to 5° C., 4 to 15° C., 4 to 13° C., 4 to 11° C., 4 to 9° C., 4 to 7° C., or 4° C., but is not limited thereto.

In yet another aspect of the present disclosure, an embodiment of the present disclosure provides a stem cell-derived exosome surface-modified with a compound capable of binding to dopamine receptors or L-amino acid transporters, wherein the exosome has a targeting ability for dopaminergic neurons and has a neuroprotective activity.

In an embodiment of the present disclosure, the stem cell-derived exosome may be surface-modified through one or more chemical bonds selected from the group consisting of ionic bonds, covalent bonds, metal bonds, coordination bonds, hydrogen bonds, and intermolecular forces between exosome surface proteins and the compound capable of binding to dopamine receptors or L-amino acid transporters; or hydrophobic insertion of amphiphilic compound bound to the compound capable of binding to dopamine receptors or L-amino acid transporters into phospholipid bilayer of the exosome.

In an embodiment of the present disclosure, when the term "comprising" is used, it means that other components may be further included, rather than excluding other components unless otherwise stated. The term "step of (to)" or "step of" used throughout the specification of the present disclosure does not mean "step for."

Hereinafter, to aid understanding of the present disclosure, preferable examples will be provided. However, the following examples are merely provided to more easily understand the present disclosure, and the scope of the present disclosure is not limited to the following examples.

EXAMPLES

Example 1. Extraction of Exosomes from Human Adipose-Derived Stem Cells

Human adipose-derived stem cell-derived exosomes were extracted during a procedure of culturing human adipose-derived stem cells. Specifically, human adipose-derived stem cells were cultured in a normal culture medium (Gibco, Cat #: 11995065) and replaced with serum-free, antibiotic-free, phenol red-free medium (Gibco Cat #: 31053028) 24 hours before the extraction of exosomes. After culturing for 24 hours, a supernatant was recovered from the cell culture.

The recovered cell culture supernatant was centrifuged at 2,000×g and 4° C. for 5 minutes, and cell debris and waste were removed through filtration using a 2 μm bottom filter. The solution recovered after filtration was isolated and purified by Tangential Flow Filtration (TFF) using a 300 k membrane filter.

Example 2. Surface Modification of Exosomes Using Compound Capable of Binding to Dopamine Receptors or L-Amino Acid Transporters The human adipose-derived stem cell-derived exosomes extracted in Example 1 were surface-modified by chemical bonding. Specifically, the exosomes were synthesized through a reaction between a carboxyl group of an exosome surface protein and an amine group of dopamine or a dopamine precursor. 20 μl of 200 mM N-Hydroxysulfosuccinimide (Sulfo-NHS) and 20 μl of 20 mM 1-ethyl-3-(3-dimethylamino-propyl) carbodiimide (EDC) were added to 200 μg/ml of exosomes dispersed in PBS and stirred for 30 minutes for activation. Thereafter, 20 μl of 200 mM dopamine or levodopa (L-DOPA) as dopamine precursor was added and stirred at 4° C. for 6 hours. After the reaction, unreacted Sulfo-NHS, EDC, and dopamine or dopamine precursors were removed using a 0.45 μm syringe filter and a PD-10 column Human adipose-derived stem cell-derived exosomes surface-modified with dopamine through the above procedure were named DP-EXO, human adipose-derived stem cell-derived exosomes surface-modified with dopamine precursor were named LD-EXO, and non-modified human adipose-derived stem cell-derived exosomes used as a control group were named AD-EXO.

Then, the particle size and morphology were analyzed through dynamic light scattering (DLS) and transmission electron microscopy (TEM), and the particle concentration was identified through nanoparticle tracking analysis (NTA).

Figure 2A:
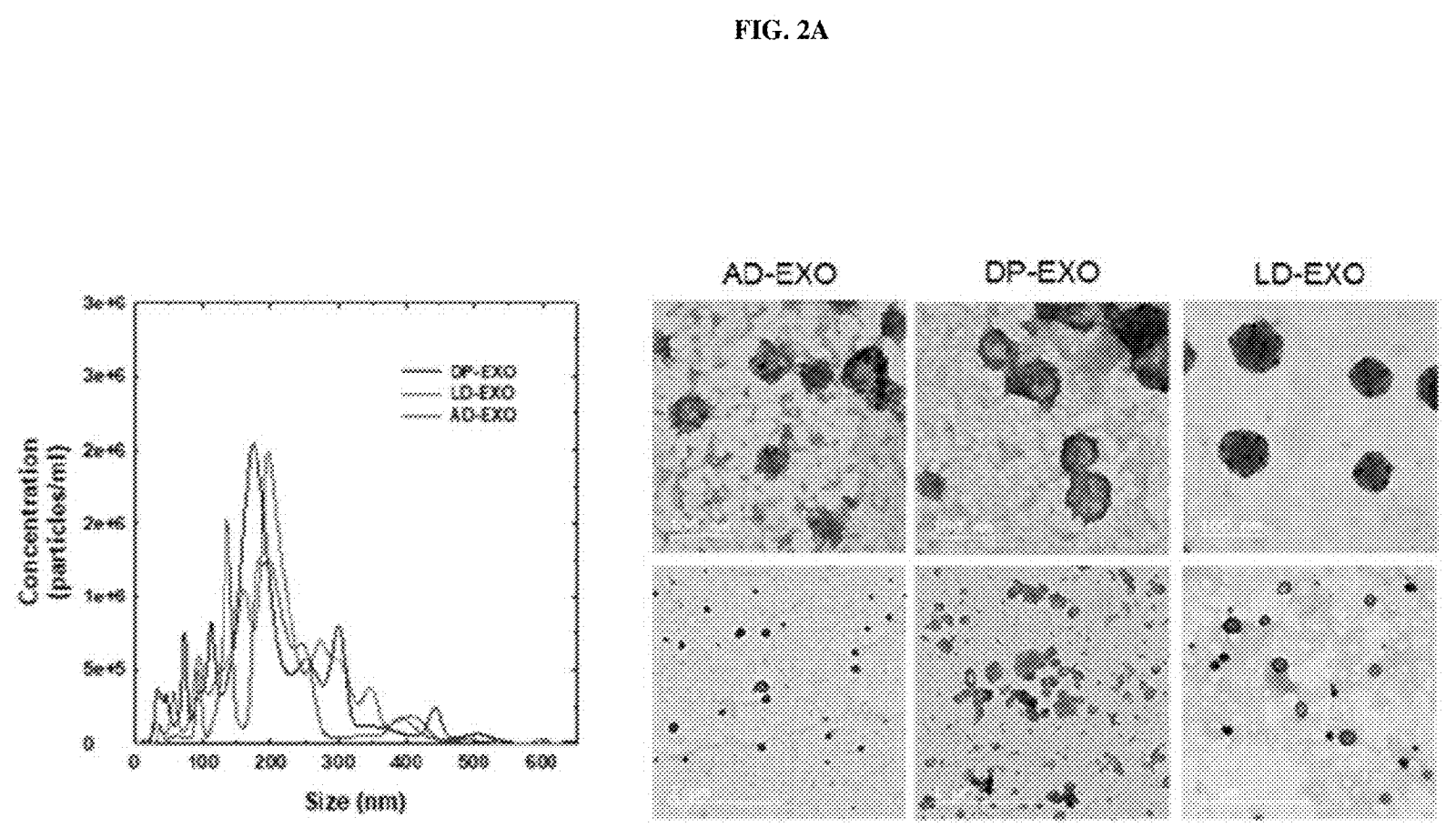

As a result of analyzing the particle size and shape before and after modification of the stem cell-derived exosome control group (AD-EXO) and the stem cell-derived exosomes surface-modified with dopamine or a dopamine precursor (DP-EXO, LD-EXO), as shown in FIG. 2A, it was identified that there was no significant difference before and after modification.

In addition, the modification of exosomes and the dopamine content on the surface were identified by ELISA. Specifically, a 96-well plate was coated with 2 μg/ml of anti-dopamine antibody by incubation at room temperature for 16 hours at 4° C. After washing the plate three times with PBST (phosphate-buffered saline with 0.05% Tween 20), a blocking buffer was added and incubated for 2 hours at room temperature. After washing three times with PBST, serial dilution of dopamine standards and diluted samples (0.33 μg/ml of protein) were added and left at room temperature for 2 hours. After washing three times with PBST, biotinylated dopamine detection antibody was added and incubated for 2 hours at room temperature. Again, the plate was washed three times, and 40-fold diluted streptavidin-conjugated peroxidase (Streptavidin-HRP) was added, followed by incubation at room temperature for 20 minutes. Then, it was washed three times with PBST, and a substrate solution in which $H_2O_2$ and tetramethylbenzidine were mixed 1:1 was added to each well, incubated for 20 minutes, and then the reaction was stopped by adding 2N $H_2SO_4$. Then, absorbance at 450 nm was measured using a microplate reader.

Figure 2B:
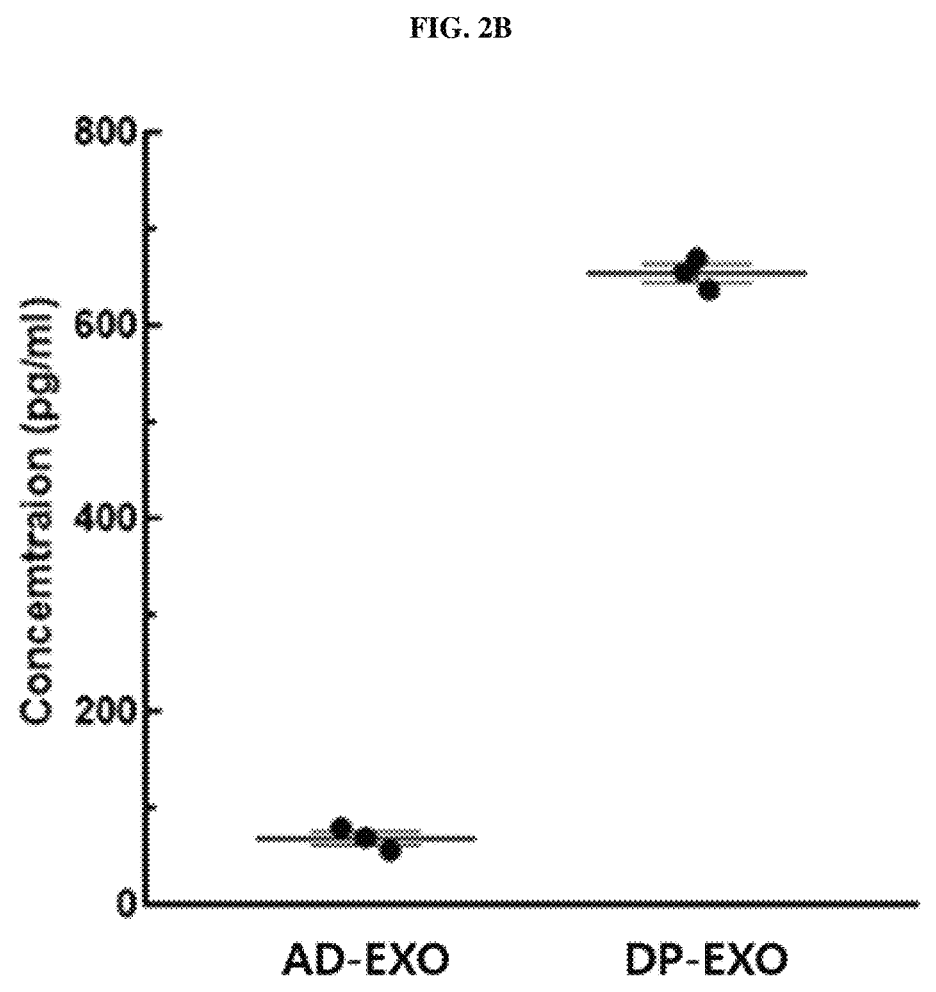

As a result, it was identified that 2.2 ng/μg of dopamine was conjugated to the modified exosome surface, as shown in FIG. 2B.

Example 3. Evaluation of Surface-Modified Exosomes for Ability to Target Neurons The fluorescence-stained exosomes of DP-EXO prepared in Example 2 were treated with SH-SY5Y and primary neurons to evaluate their ability to target dopamine receptor-expressing cells.

Specifically, the exosomes before modification were mixed with Cy5.5-NHS at a weight ratio of 200:1, stirred at 4° C. for 4 hours, and the modification stage after staining was performed as in Example 2 above. After seeding at a density of $2×10^5$ cells in a 6-well plate with a confocal dish and cover glass, SH-SY5Y cells were cultured for 48 hours and primary neurons were cultured for one week. The fluorescence of exosomes was quantified and processed using Nanodrop, and visualized using confocal laser scanning microscopy (CLSM).

Figure 3A:
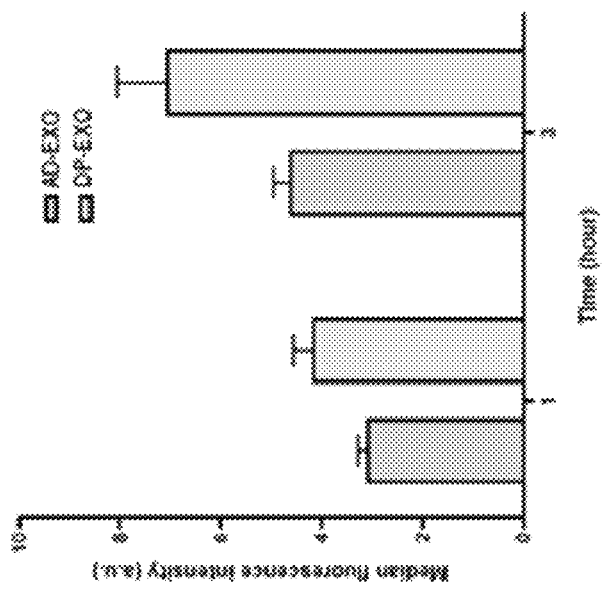
FIG. 3A is a diagram identifying the cell uptake behavior over time of a stem cell-derived exosome surface-modified with dopamine in dopamine receptor-expressing cells according to an embodiment of the present disclosure.
Figure 3A:
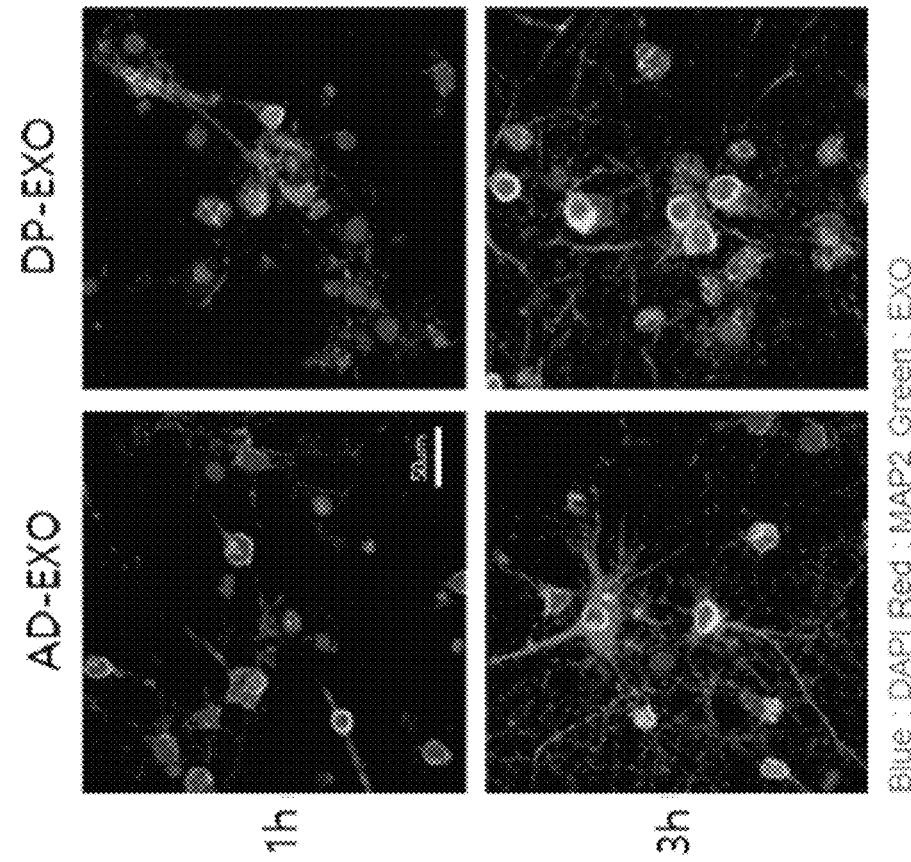

As a result of measuring the exosome uptake behavior of the stem cell-derived exosome control group (AD-EXO) and the stem cell-derived exosome surface-modified with dopamine (DP-EXO) over time in SH-SY5Y cells, as shown in FIG. 3A, compared to AD-EXO, when DP-EXO surface-modified with dopamine was treated, a higher amount of Cy5.5 fluorescence (green) appeared after one and three hours of exosome treatment.

Figure 3B:
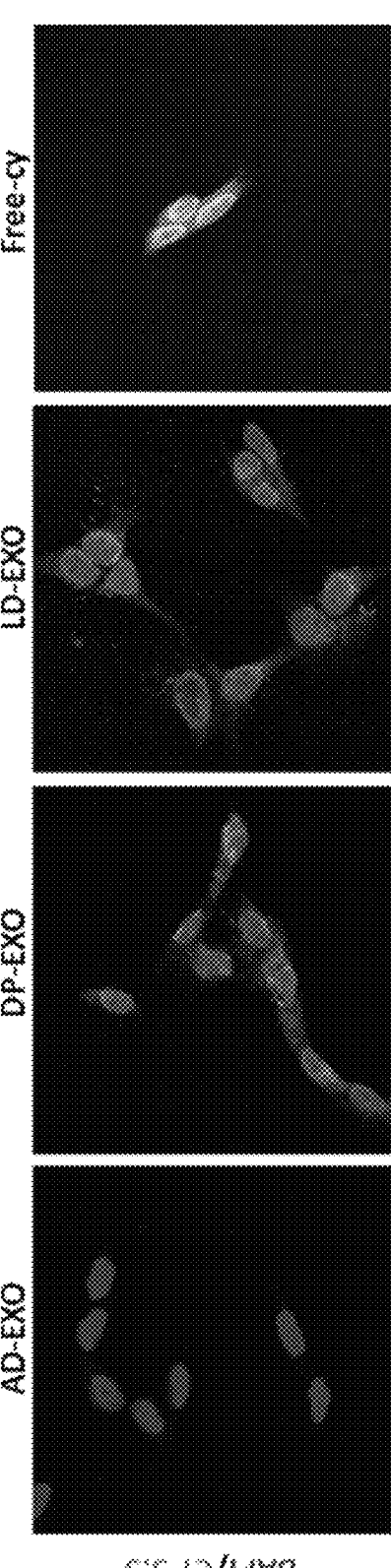
FIG. 3B is a diagram identifying the cell uptake behavior of a stem cell-derived exosome surface-modified with a compound capable of binding to dopamine receptors or L-amino acid transporters in dopamine receptor-expressing cells according to an embodiment of the present disclosure.

In addition, as a result of observing the cell uptake behaviors in dopamine receptor-expressing cells for the stem cell-derived exosome control group (AD-EXO) and the stem cell-derived exosome surface-modified with dopamine or dopamine precursors (DP-EXO, LD-EXO) in SH-SY5Y cells, as shown in FIG. 3B, Cy5.5 fluorescence (red) appeared in the DP-EXO and LD-EXO-treated groups.

Figure 3C:
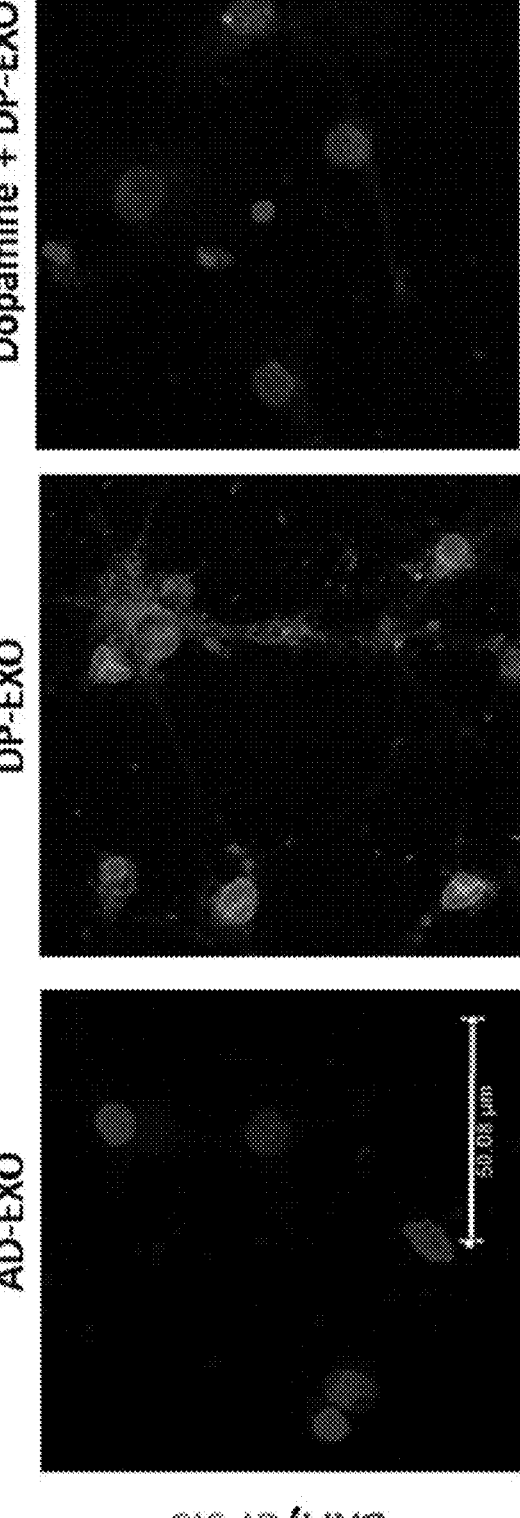
FIG. 3C is a diagram identified by comparing the cell uptake behavior of a stem cell-derived exosome surface-modified with dopamine in dopamine receptor-expressing cells according to an embodiment of the present disclosure with the case where the unmodified exosome control group and the cells pretreated with dopamine are treated with a stem cell-derived exosome surface-modified with dopamine.

As a result of observing the cell uptake behavior in the stem cell-derived exosome control group (AD-EXO), stem cell-derived exosome surface-modified with dopamine (DP-EXO), and DP-EXO-treated group of cells pretreated with 200 μM of dopamine for one hour in primary neurons, as shown in FIG. 3C, it was identified that the fluorescence (red) of Cy5.5 was insufficient in the DP-EXO-treated group and the AD-EXO-treated group of cells pretreated with dopamine.

From the above results, it was identified that DP-EXO and LD-EXO were effectively absorbed into cells by binding to dopamine receptors.

Example 4. Evaluation of Neuroprotective Efficacy of Surface-Modified Exosomes DP-EXO prepared in Example 2 was treated with a Parkinson's disease cell model to evaluate the neuroprotective efficacy.

Specifically, primary neurons were isolated from SD rat embryos (TP-17), and differentiated into neurons. Then, a Parkinson's disease cell model most clinically similar to Parkinson's disease was induced by treating preformed-fibril (PFF) to form alpha synuclein aggregates (p-a-syn). Exosomes were quantified with NTA and treated with $10^5$, $10^6$, $10^7$, and $10^8$/ml once every two days for a total of 14 days from the day of PFF treatment, and the survival rate was identified through MTT analysis and PI staining.

Figure 4:
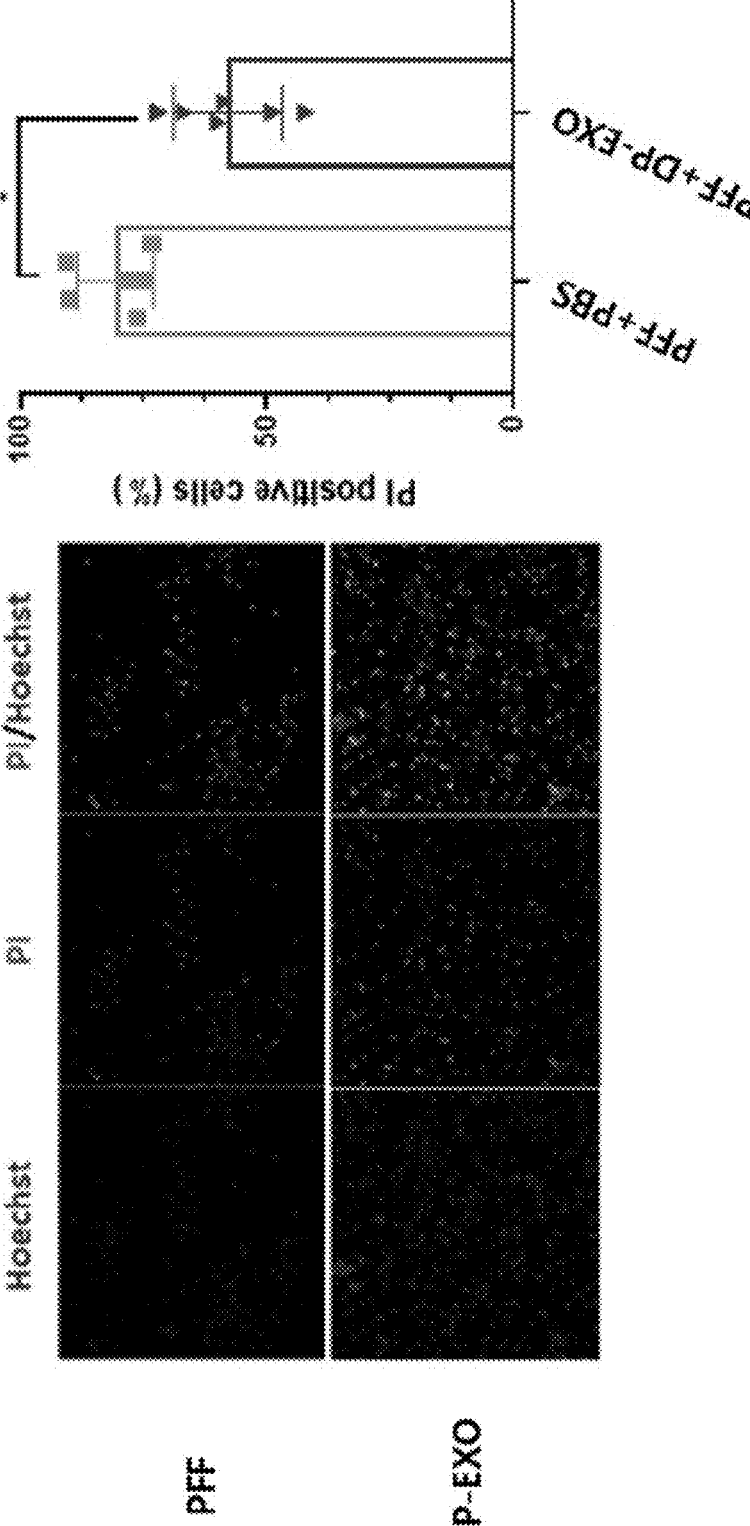
FIG. 4 is a diagram identifying the apoptosis reduction effect by treatment with a stem cell-derived exosome surface-modified with dopamine in a Parkinson's disease cell model according to an embodiment of the present disclosure.

As described above, as a result of PI staining, a method used to measure apoptosis after treating stem cell-derived exosomes surface-modified with dopamine (DP-EXO) at $10^8$/ml in an in vitro Parkinson's disease model induced by treating primary neurons with PFF, as shown in FIG. 4, it was identified that the number of PI-positive cells decreased during DP-EXO treatment, and apoptosis was reduced.

Figure 5:
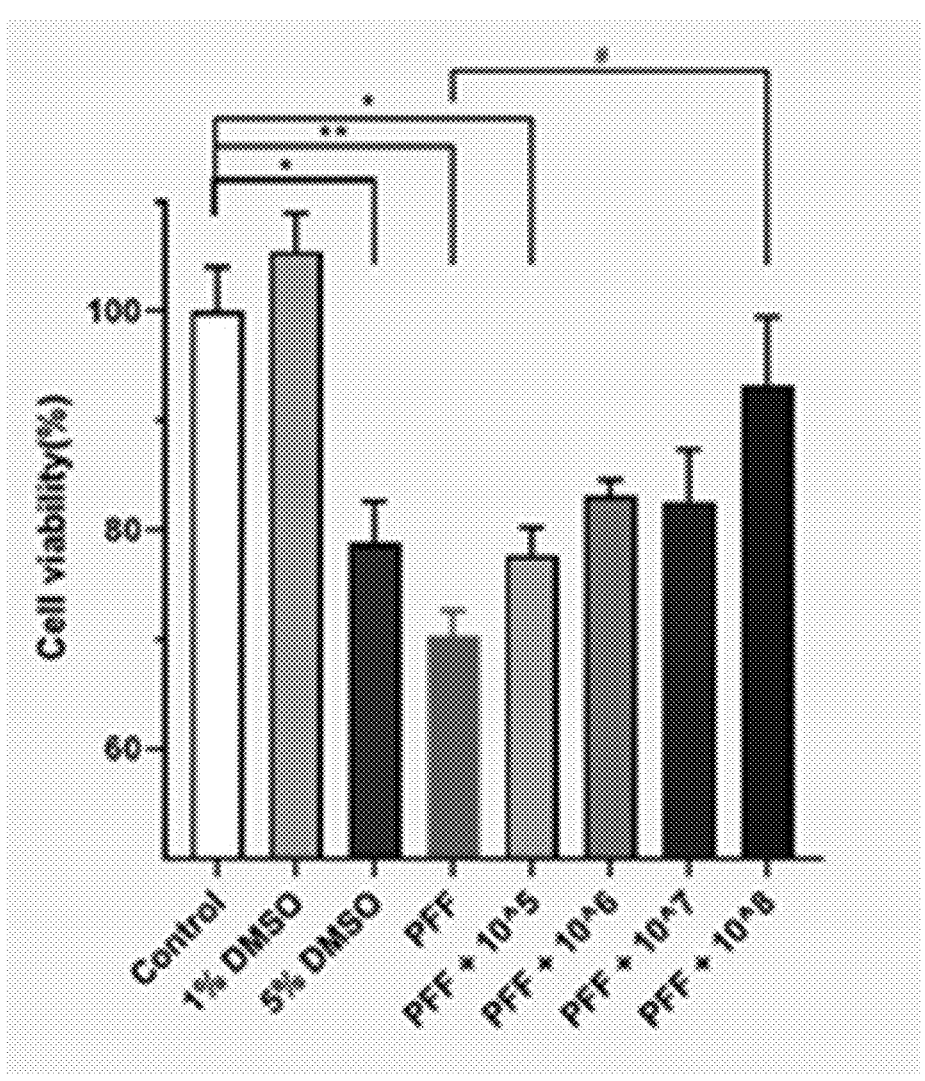
FIG. 5 is a diagram identifying the effect of restoring cell viability by treatment with a stem cell-derived exosome surface-modified with dopamine in a Parkinson's disease cell model according to an embodiment of the present disclosure.

In addition, as a result of observing the neuron protective efficacy by treatment with stem cell-derived exosomes surface-modified with dopamine (DP-EXO) in an in vitro Parkinson's disease model induced by treating primary neurons with PFF by exosome concentration through MTT analysis, as shown in FIG. 5, it was identified that in the cells treated with PFF, the viability decreased to 70%, whereas in the cells treated with DP-EXO, the cell viability was recovered in proportion to the exosome concentration compared to the group treated with PFF alone.

Figure 6:
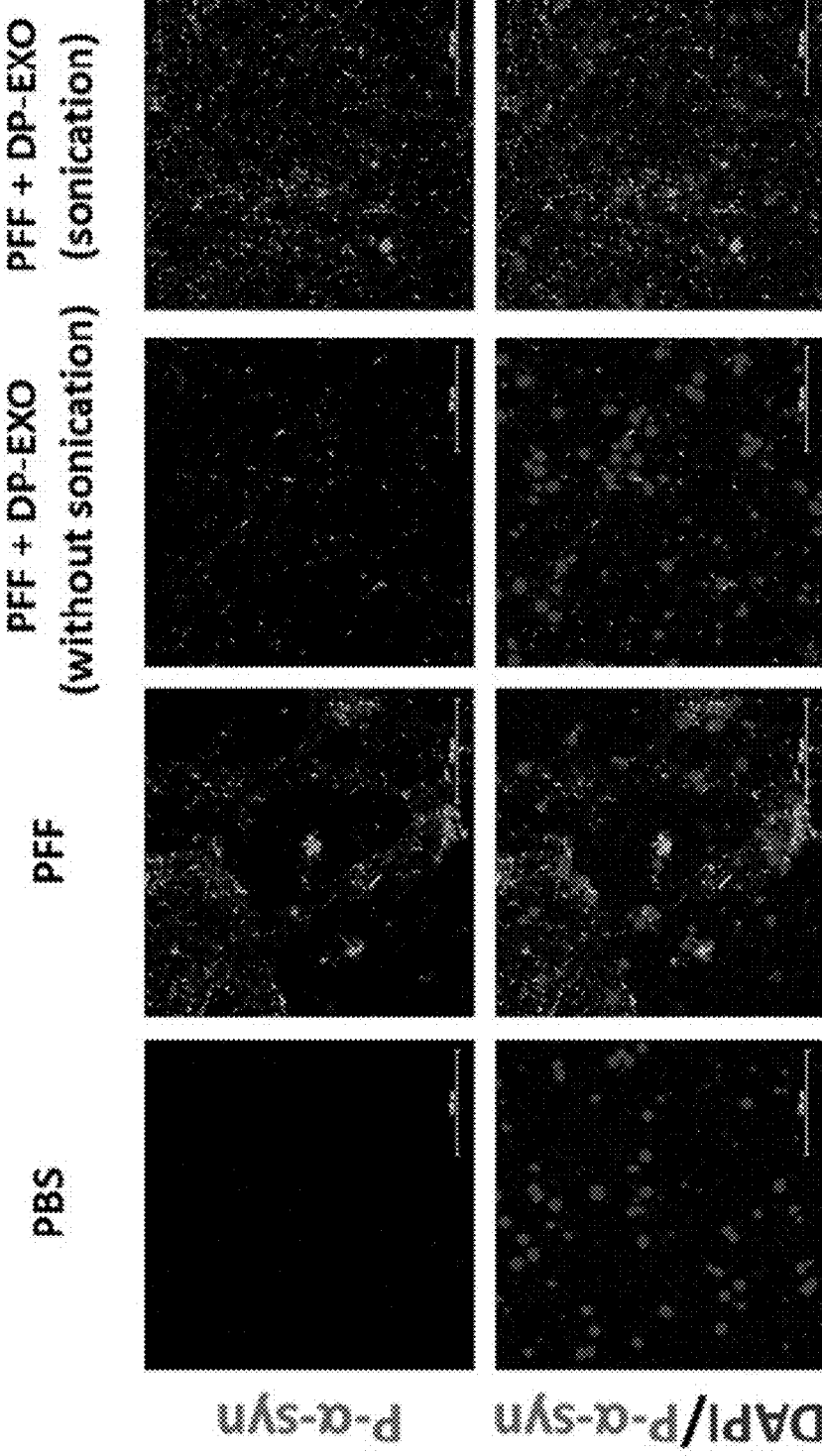
FIG. 6 is a diagram identifying that the effect of inhibiting alpha-synuclein hyperphosphorylation disappears due to exosomal degradation when ultrasonic treatment is applied to a stem cell-derived exosome surface-modified with dopamine in a Parkinson's disease cell model according to an embodiment of the present disclosure.

Meanwhile, when hyperphosphorylation of alpha synuclein, a marker of Parkinson's disease, was induced in an in vitro Parkinson's disease model induced by treating primary neurons with 1 mg/ml of PFF, as shown in FIG. 6, it was identified that hyperphosphorylation of alpha synuclein was inhibited when treated with DP-EXO in a PFF-induced Parkinson's disease model, and that the inhibitory effect of alpha-synuclein hyperphosphorylation of these exosomes disappeared when DP-EXO exosomes were sonicated and degraded.

Therefrom, it was found that the Parkinson's disease inhibitory effect of exosomes surface-modified with dopamine was exosome-dependent.

Figure 7:
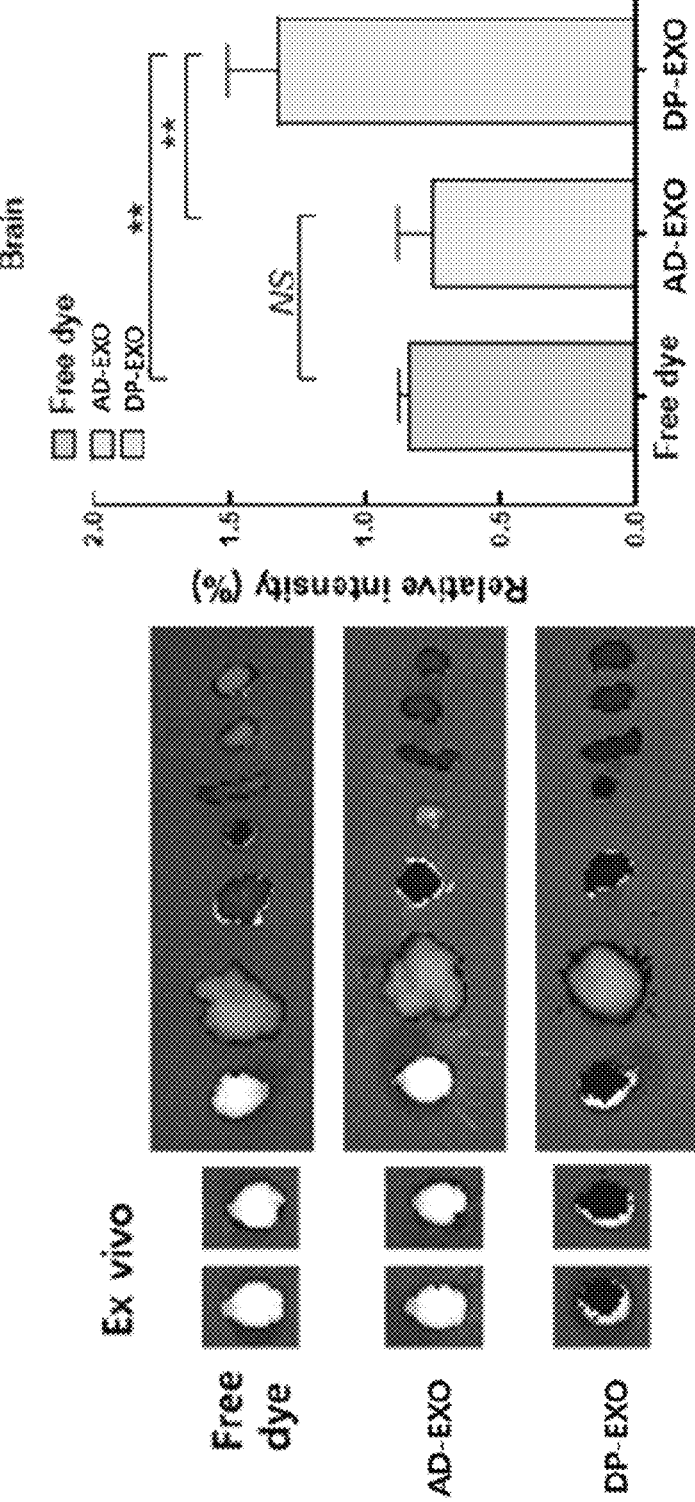
FIG. 7 is a diagram identifying the internal circulation behavior of a stem cell-derived exosome surface-modified with dopamine according to an embodiment of the present disclosure.

In addition, after administering $10^8$/ml of fluorescently stained stem cell-derived exosome control group (AD-EXO) and surface-modified stem cell-derived exosome (DP-EXO) to C67/BL6 mice, their internal circulation behavior was observed. As a result, as shown in FIG. 7, it was identified that migration to the brain and accumulation in the brain increased in the group treated with DP-EXO compared to the group treated with free dye and AD-EXO.

The stem cell-derived exosome according to the present disclosure is surface-modified with a compound capable of binding to dopamine receptors or L-amino acid transporters, and selectively binds to dopamine receptors (D2) overexpressed as autoreceptors in dopaminergic neurons in the substantia nigra through surface modification of exosomes. Thereby, local accumulation in dopaminergic neurons is possible. Accordingly, it was identified that stem cell-derived exosomes solved the issue of difficulty in efficient intracerebral delivery of exosome therapeutic agents for brain diseases because in general, when injected into the body, less than 1% of Naïve exosomes reach the brain, and exhibited an excellent neuroprotective effect and neuron death inhibitory effect. Accordingly, the surface-modified stem cell-derived exosome according to the present disclosure is expected to be usefully used as a composition for preventing or treating a brain disease including Parkinson's disease and Alzheimer's disease.

The above description of the present disclosure is provided for the purpose of illustration, and it would be understood by those skilled in the technical field to which the present disclosure pertains that the present disclosure may be embodied in other specific forms without changing technical ideas or essential features of the present disclosure. Thus, it is clear that the above-described embodiments are illustrative in all aspects and do not limit the present disclosure.

What is claimed is:

1. A method for treating or alleviating a brain disease, comprising administering to a subject in need thereof a composition comprising, as an active ingredient, a stem cell-derived exosome surface-modified with a compound capable of binding to dopamine receptors or L-amino acid transporters, wherein the surface-modified exosome comprises a linker that binds the compound to the exosome surface, wherein the brain disease is one or more selected from the group consisting of Parkinson's disease, Alzheimer's disease, dementia, Huntington's disease, amyotrophic lateral sclerosis, multiple sclerosis, Creutzfeldt-Jakob disease, Pick disease, and Lewy body disease.

2. The method of claim 1, wherein the stem cells are one or more selected from the group consisting of adipose-derived stem cells, umbilical cord blood stem cells, bone marrow stem cells, neural stem cells, muscle stem cells, skin stem cells, and amnion stem cells.

3. The method of claim 1, wherein the compound capable of binding to dopamine receptors or L-amino acid transporters is dopamine or a dopamine precursor.

4. The method of claim 3, wherein the dopamine precursor is one or more selected from the group consisting of levodopa (L-dopa), L-phenylalanine, L-tyrosine, phenylethylamine, and tyramine.

5. The method of claim 1, wherein the stem cell-derived exosome has a targeting ability for dopaminergic neurons.

6. The method of claim 1, wherein the stem cell-derived exosome has a neuroprotective activity.

7. The method of claim 1, wherein the stem cell-derived exosome is surface-modified through one or more chemical bonds selected from the group consisting of ionic bonds, covalent bonds, metal bonds, coordination bonds, hydrogen bonds, and intermolecular forces between exosome surface proteins and the compound capable of binding to dopamine receptors or L-amino acid transporters; or hydrophobic insertion of amphiphilic compound bound to the compound capable of binding to dopamine receptors or L-amino acid transporters into phospholipid bilayer of the exosome.

8. The method of claim 1, wherein the compound capable of binding to dopamine receptors or L-amino acid transporters is bound to a surface of the exosome at a dry weight ratio of 1:0.0005 to 0.005 (the exosome:the compound capable of binding to dopamine receptors or L-amino acid transporters) with respect to a dry weight of the exosome.

* * * * *